United States Patent [19]

Niederer et al.

[11] 4,430,761
[45] Feb. 14, 1984

[54] JOINT ENDOPROSTHESIS

[75] Inventors: Peter G. Niederer, Zollikofen; Otto Frey, Winterthur, both of Switzerland

[73] Assignee: Sulzer Brothers Limited, Winterthur, Switzerland

[21] Appl. No.: 317,746

[22] Filed: Nov. 3, 1981

[30] Foreign Application Priority Data

Feb. 19, 1981 [CH] Switzerland .................. 1091/81

[51] Int. Cl.³ .................................. A61F 1/24
[52] U.S. Cl. ........................... 3/1.91; 3/1.913; 128/92 C; 128/92 CA
[58] Field of Search ................... 3/1.9–1.913; 128/92 C, 92 CA

[56] References Cited

U.S. PATENT DOCUMENTS

| 3,816,854 | 6/1974 | Schlein | 128/92 C X |
| 3,965,490 | 6/1976 | Murray et al. | 3/1.913 |
| 4,199,824 | 4/1980 | Niederer | 3/1.913 |
| 4,310,931 | 1/1982 | Muller | 128/92 CA X |

FOREIGN PATENT DOCUMENTS 989341  5/1951  France ............................. 3/1.913

Primary Examiner—Ronald L. Frinks
Attorney, Agent, or Firm—Kenyon & Kenyon

[57] ABSTRACT

The shank of the prosthesis is provided with a plurality of parallel grooves in order to improve adhesion of the shank in a prepred bone cavity. The grooves are used to improve adhesion either directly to bone tissue or to a cement bed within a bone cavity. The grooves are spaced apart on a center-line to center-line distance of a few millimeters and each has a depth of several tenths of a millimeter.

2 Claims, 4 Drawing Figures

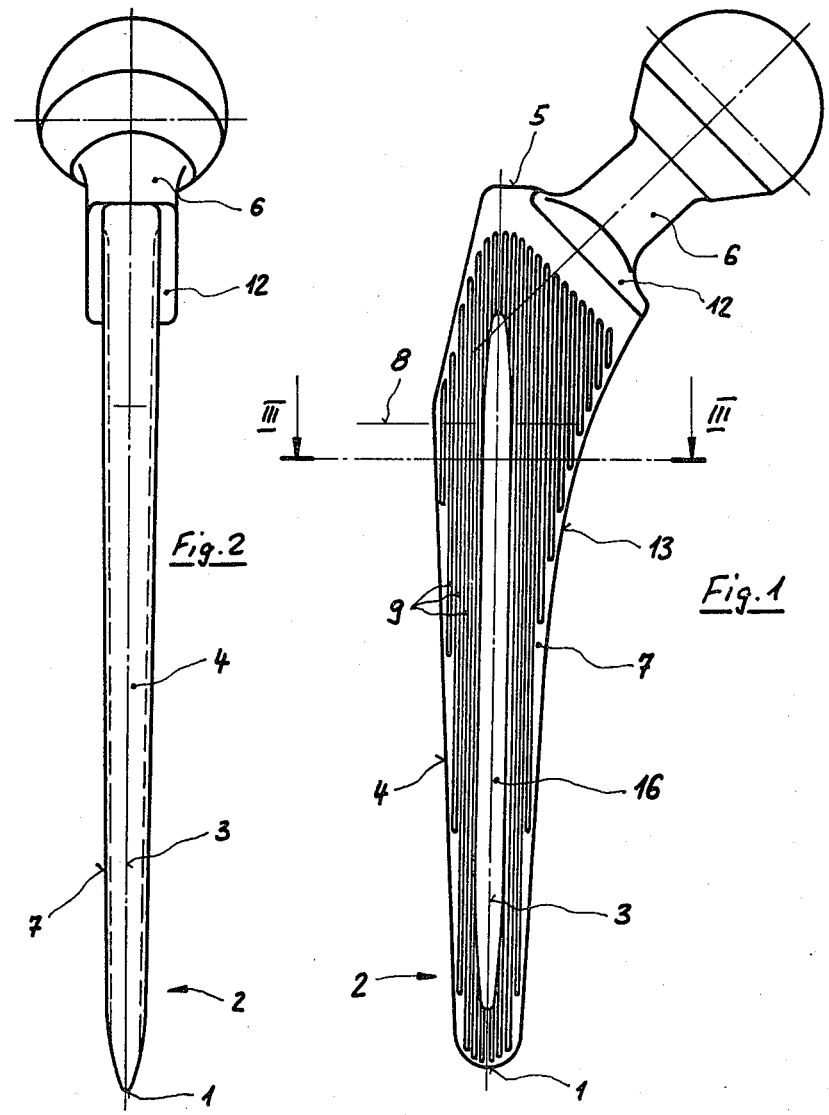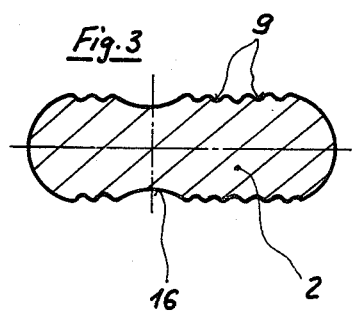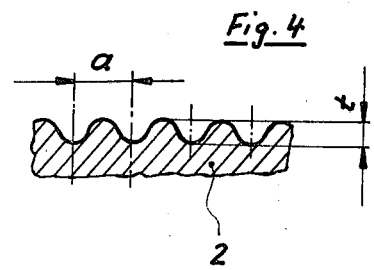

JOINT ENDOPROSTHESIS

This invention relates to a joint endoprosthesis. More particularly, this invention relates to a blade-type shank for a joint endoprosthesis such as a hip joint prosthesis.

Heretofore, various types of joint endoprosthesis have been known for implanting in bones in order to form a joint. For example, in some cases, the prostheses have been formed with a straight blade type shank for anchoring as by a wedging action and through a cement bed in a bone. In case of a hip joint prosthesis, the shank usually widens conically from a free distal end symmetrically of a longitudinal median axis of the shank on all sides and then, at a point about three-quarters along the shank, bevels inwardly along the narrow lateral side towards the shank axis. The opposite narrow medial side, in some cases, passes along a smooth curve in stepless manner to a collar which separates the shank from a neck of the prosthesis.

Hip joint prostheses of this kind are known, for example from the journal Orthöpade (8 1979), pages 73-74, and in particular FIG. 1. The so-called straight shank of this prosthesis is intended to be wedged in a hollow space of a medullary cavity which has been surgically matched to the shank and which is usually filled with a bed of bone cement in such a way that the cement bed or cement quiver is largely relieved from carrying loads. The carrying support of this prosthesis takes place primarily by wedging in along the narrow medial and lateral sides of the shank and by adaptation of the smooth curve of the medial narrow side of the calcarine arc situated medially in the femur.

It, however, has been found in clinical practice that it is necessary to improve the adhesion of these straight shank prostheses which are either hammered into a cavity without cement or driven into a bone cement quiver. This is because it may happen, for example, when the shank is fixed via a cement quiver, that the cement bed, although closed along the periphery, is displaced during the implantation operation in the circumferential direction and especially in the region of the medial narrow side. Further, the cement still being soft, can slide along the shank relatively easily.

Accordingly, it is an object of the invention to improve the adhesion between a straight shank endoprosthesis in a bone or cement bed.

It is another object of the invention to facilitate the implantation of a straight shank endoprosthesis in a bone.

Briefly, the invention is directed to a joint endoprosthesis having a shank with a blade like portion formed with a narrow lateral side, a narrow medial side, a pair of side walls and an arcuate side extending from the medial side. In addition, the side walls as well as the lateral and medial sides extend along a longitudinal median axis from a distal end with a conical taper symmetrically of the axis. In accordance with the invention, the shank is provided with a plurality of grooves in the side walls, which grooves extend in direction of the longitudinal median axis of the shaft and parallel to the side walls.

The endoprosthesis is also formed with a neck which is disposed angularly relative to the axis of the shank and a collar which separates the shank from the neck.

When the shank is anchored in a cement bed in a surgically prepared femur, the grooves impede and make difficult any flowing of the cement. Further, in the case of a cementless anchoring, the grooves impede and make difficult a flow of fragments of the spongy bone tissue which is created by a hammering in action. In addition, the area available for adhesion on the side walls of the shank is enlarged. This, of course, improves the adhesion of the shank to the bone or bone cement.

As is known, lateral reeling and/or rotation movements, which are inevitable during an axial insertion of a prosthesis shank, cause a slight local widening of the cement bed. As a result, since the bone cement is plastic and not elastic, the cement does not adhere to the shank in the region of these widenings. However, since the grooves of the shank extend conically with the shank surfaces, such widenings are eliminated by a local removal or displacement of the bone cement.

It has been found that for shanks for hip joint prostheses, an especially good adhesion has resulted experimentally when the depth of each groove is between 0.2 to 0.5 millimeters with a center-line to center-line spacing between the grooves of from 0.5 to 2.0 millimeters.

These and other objects and advantages of the invention will become more apparent from the following detailed description taken in conjunction with the accompanying drawings wherein:

FIG. 1 illustrates a hip joint prosthesis constructed in accordance with the invention;

FIG. 2 illustrates a side view of the prosthesis of FIG. 1;

FIG. 3 illustrates a view taken on line III—III of FIG. 1; and

FIG. 4 illustrates an enlarged detailed view of FIG. 3.

Referring to FIGS. 1 and 2, the joint endoprosthesis is constructed as a hip joint prosthesis. In this regard, the prosthesis has a shank 2 with a blade-like portion formed with a narrow lateral side 4, a narrow medial side 13 and a pair of side walls 7. As indicated in FIG. 1, each side wall 7 of the shank 2 widens from the distal end 1 with a conical taper at first symmetrically to the vertical (straight) longitudinal median axis 3 of the shank 2. In addition, the lateral side 4 is inclined inwardly at an upper end, as viewed, towards the longitudinal median axis 3 and terminates in an, at least, almost horizontal shoulder 5, as viewed. At about mid-height of the shank 2, the medial side 13 changes over into an arcuate portion which extends away from the longitudinal median axis 3, for example on a circular arc. This arcuate portion terminates in a stepless manner in a collar 12 which separates the shank 2 from a neck 6. As shown in FIG. 1, the neck 6 is angularly disposed relative to the longitudinal axis 3 of the shank 2 and carries a spherical joint head of conventional construction.

As indicated in FIG. 1, the side walls 7 of shank 2 are closed off at the distal end 1 by a circular transition from the lateral side 4 to the medial side 13 while, in the perpendicular direction as shown in FIG. 2, the side walls 7 terminate with relatively large radii in a point. The curvature at the distal end 1 is chosen, to the extent possible, so that a steady transition of the load-applying dynamic flow occurs from the shank 2 onto a surrounding cement quiver and/or bone tissue which may be compacted by a driving in of the prosthesis into a cavity of a bone.

As can be seen in FIG. 2, not only do the side walls 7 of the shank 2 widen conically from the distal end 1 but also the lateral side 4 and medial side 13 extend along the longitudinal median axis 13 with a conical taper symmetrically of the axis 3. In this case, the angle of taper for the lateral side 4 and medial side 13 is very small, for example 0.5° to 1.5° relative to the vertical axis 3. Further, the taper of the narrow sides 4, 13 extends to a level 8 which is about ¾ of the length of the shank 2 from the distal end 1. Above this level 8, the lateral limitations of the sides 4, 13 and, hence, the side walls 7 extend parallel to each other.

Referring to FIGS. 1 and 3, at least the surface of each side wall 7 of the shank 2 is provided with a longitudinally extending depression 16 which extends parallel to the longitudinal median axis 3 and parallel to the shank surface. In addition, each of the side walls 7 is provided with a plurality of small grooves or ruts 9 which extend parallel to the longitudinal median axis 3 and the surfaces of the side walls 7. For the sake of simplicity, the longitudinal depressions 16 are not provided with grooves 9. However, a portion of the upper areas of each of the side walls 7 is provided with the grooves 9. It is, of course, possible to provide the longitudinal depression 16 with grooves 9. Likewise, the upper portion of each side wall 7 may be kept free from the grooves 9 without any important reduction in the improved adhesion.

Referring to FIG. 4, the grooves 9 are spaced apart from each other a distance a, from center-line to center-line, of from 0.5 to 2.0 millimeters. In addition, the depth t of each groove is from 0.2 to 0.5 millimeters. These dimensions have been found to be particularly effective for a hip joint prosthesis.

The shank 2 of the prosthesis can be made of any suitable material such as a metal or metal alloy as is known. In the case of a metal shank 2, the grooves 9 may be made, for example by mill-cutting.

The invention this provides an endoprosthesis with an improved means for adhering the prosthesis in a bone cavity. Further, this means may be readily incorporated into the shank of the prosthesis in relatively simple manner.

What is claimed is:

1. A joint endoprosthesis comprising
   a shank having a blade-like portion formed with a smooth narrow lateral side, a smooth narrow medial side and a pair of side walls, each said side wall widening along a straight longitudinal median axis from a distal end with a conical taper symmetrically of said axis, said medial side having an arcuate portion extending away from said median axis; and
   a plurality of parallel longitudinally extending grooves being straight along the entire length thereof in each said side wall, said grooves extending in the direction of said axis parallel to said side walls and being spaced apart a distance from center-line to center-line of from 0.5 to 2.0 millimeters with each groove having a depth of from 0.2 to 0.5 millimeters to impede a flow of cement or fragments of spongy bone tissue during implantation.

2. A joint endoprosthesis as set forth in claim 1 wherein said lateral side and said medial side taper symmetrically for about three-quarters of the length of said shank from said distal end.

* * * * *

UNITED STATES PATENT AND TRADEMARK OFFICE
CERTIFICATE OF CORRECTION

PATENT NO. : 4,430,761
DATED : February 14, 1984
INVENTOR(S) : Peter Gino Niederer, et al.

It is certified that error appears in the above—identified patent and that said Letters Patent is hereby corrected as shown below:

On the title page,

Correct the assignee from "Sulzer Brothers Limited, Winterthur Switzerland " to - Sulzer Brothers Limited Winterthur, Switzerland, Protek A.G. Berne, Switzerland -

Signed and Sealed this

Thirty-first Day of July 1984

[SEAL]

Attest:

GERALD J. MOSSINGHOFF

Attesting Officer

Commissioner of Patents and Trademarks